US006813014B2

(12) United States Patent
Hong et al.

(10) Patent No.: US 6,813,014 B2
(45) Date of Patent: Nov. 2, 2004

(54) METHOD FOR DESIGNING AND TUNING AND SYSTEM FOR MEASURING A REFRACTIVE INDEX OF A MAGNETIC FLUID

(76) Inventors: Chin-Yih Rex Hong, 4F, No. 31, Lane 57, Ta Tze St., Ta Tze, Taipei 104 (TW); Herng-Er Horng, 4F, No. 31, Lane 57, Ta Tze St., Ta Tze, Taipei 104 (TW); Hong-Chang Yang, 4F, No. 31, Lane 57, Ta Tze St.., Ta Tze, Taipei 104 (TW); Shieh-Yueh Yang, 3F, No. 8-1, Sec. 2, Huan-Ho E Rd., Taipei 234 (TW); Wan-Sun Tse, 4F, No. 16, Alley 47, Lane 70, Sec. 2, Yenchiu-Yuan Rd., Taipei (TW)

( * ) Notice: Subject to any disclaimer, the term of this patent is extended or adjusted under 35 U.S.C. 154(b) by 339 days.

(21) Appl. No.: 10/125,249
(22) Filed: Apr. 16, 2002
(65) Prior Publication Data
US 2003/0193663 A1 Oct. 16, 2003

(51) Int. Cl.$^7$ .............................................. G01N 21/41
(52) U.S. Cl. ........................ 356/128; 356/134; 356/135
(58) Field of Search .................................. 356/128–137

(56) References Cited

U.S. PATENT DOCUMENTS 6,086,780 A * 7/2000 Hong et al. .............. 252/62.52

* cited by examiner

Primary Examiner—Gregory J. Toatley, Jr.
Assistant Examiner—Amanda Merlino
(74) Attorney, Agent, or Firm—J. C. Patents (57) ABSTRACT

A method for designing and tuning a refractive index of a magnetic fluid is performed by adjusting some characteristic parameters. The characteristic parameters include the type of carrier, the type of magnetic particles, the concentration of the magnetic ingredient; the wavelength of an intended light onto the magnetic fluid layer; the strength of applied magnetic field; the sweep rate of the magnetic field; the direction of the applied magnetic field; the strength of applied magnetic field associated with the thickness of the magnetic fluid layer; and the strength of applied magnetic field associated with the temperature. A magnetic fluid with a designed value of refractive index under zero magnetic field is synthesized by carefully selecting the carrier and the volume concentration of the magnetic particles, and this value can further be tuning around the designed value by changing the forgoing characteristic parameters.

2 Claims, 13 Drawing Sheets

METHOD FOR DESIGNING AND TUNING AND SYSTEM FOR MEASURING A REFRACTIVE INDEX OF A MAGNETIC FLUID

BACKGROUND OF THE INVENTION

1. Field of Invention

The present invention relates to technology about magnetic fluids. More particularly, the present invention relates to the method of designing a magnetic fluid with a desired value of refractive index. Moreover, the refractive index of the magnetic fluid can be tuned around the designed value as needed.

2. Description of Related Art

Ferrofluids are a type of magnetic fluid that typically consisting of colloidal magnetic particles such as magnetite or manganese-zinc ferrites, disposed with the aid of surfactant in a continuous carrier phase. The average diameter of the disposed magnetic particles conventionally ranges about between 5–10 nm. Each particle has a constant magnetic dipole moment proportional to its size that can align with an external magnetic field.

Ferrofluids experience body forces in homogeneous magnetic fields, that allows their position to be manipulated and thus enable the construction of devices, such as rotary seals, bearings, and related mechanical devices. Ferrofluids can also be used in display device that uses a magnetic field to capture an opaque magnetic fluid in a pre-determined optical pattern. As the technology is continuously developed, it can be expected to have more various applications with ferrofluids in the future.

Usually, the magnetic fluid includes the magnetic particles in a fluid base. For example, the magnetic fluids include water/kerosene/heptan-based $Fe_3O_4$/$MnFe_2O_4$/$CoFe_2O_4$. Since the nature of matter, the magnetic fluid naturally has a refractive index. The refractive index is related to the properties of the magnetic fluid. If the refractive index of the magnetic fluid can be designed and tuned according to the design requirement, magnetic fluid would be more powerful for its application. However, how to design and tune the refractive index of the magnetic fluid is still not being well investigated.

SUMMARY OF THE INVENTION

The invention provides a method for forming a magnetic fluid, of which the refractive index is designed to at a desired quantity without magnetic field presented.

The invention provides a system for forming a magnetic fluid, of which the refractive index is designed to at a desired quantity without magnetic field presented.

The invention provides a method for forming a magnetic fluid, of which the refractive index is tunable to a desired quantity.

The invention provides a system for forming a magnetic fluid, of which the refractive index is tunable to a desired quantity.

The invention provides a measuring system for measuring the refractive index of the magnetic fluid base on a critical angle at which a total reflection occurs with respect to an incident light.

As embodied and broadly described herein, the invention provides a method for designing and tuning a refractive index of a magnetic fluid that is performed by adjusting some characteristic parameters. The characteristic parameters include the type of carrier, the type of magnetic particles, the concentration of the magnetic ingredient; the wavelength of an intended light onto the magnetic fluid layer; the strength of applied magnetic field; the sweep rate of the magnetic field; the direction of the applied magnetic field; the strength of applied magnetic field associated with the thickness of the magnetic fluid layer; and the strength of applied magnetic field associated with the temperature. A magnetic fluid with a designed value of refractive index under zero magnetic field is synthesized by carefully selecting the carrier, the type of magnetic particles and the volume concentration of the magnetic particles, and this value can further be tuning around the designed value by changing the forgoing characteristic parameters.

The invention also provides another method for measuring a refractive index of a magnetic fluid layer under an environment with a condition, wherein the magnetic fluid layer has a magnetic ingredient and is injected in a cell of a substrate. The method comprises putting a prism on the magnetic fluid layer, wherein a side surface against a right angle of the prism contacts with the magnetic fluid layer. The prism has a prism refractive index $n_p$. An incident light is incident onto the magnetic fluid layer through the prism with in an incident angle $\theta_i$ with respect to a normal direction. An intensity of the reflected light is measured, so as to determine whether or not a critical angle for total reflection by the magnetic fluid layer is achieved under the incident angle $\theta_i = \theta_{it}$, where $\theta_{it}$ is the value of incident angle $\theta_t$ at which the total refraction occurs at the interface between the prism and magnetic fluid layer. The refractive index of the magnetic fluid layer is determined according to a formula of $$n_{MF} = \frac{1}{2}\left(\sqrt{2n_p^2 - 2\sin^2\theta_{it}} - \sqrt{2}\sin\theta_{it}\right),$$

where $n_{MF}$ is a quantity of the refractive index of the magnetic fluid layer.

The invention also provides a system to measure a refractive index of a magnetic fluid layer, wherein the refractive index is tunable. The system comprises a substrate to hold the magnetic fluid layer, wherein the magnetic fluid layer has a magnetic ingredient in a fluid base. A measuring subsystem to measure the refractive index of the magnetic fluid layer, wherein the measuring system allows the refractive index to be tuned under at least one of a plurality of measuring conditions. The conditions comprise the type of carrier, the type of magnetic particles, the concentration of the magnetic ingredient; the wavelength of an intended light onto the magnetic fluid layer; the strength of applied magnetic field; the sweep rate of the magnetic field; the direction of the applied magnetic field; the strength of applied magnetic field associated with the thickness of the magnetic fluid layer; and the strength of applied magnetic field associated with the temperature.

In the foregoing measuring subsystem, it measures the refractive index of the magnetic fluid layer according to a critical angle for total reflection with respect to an incident light.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Currently, it has not been reported in the prior art yet about how to design a magnetic fluid with a desirable refractive index and to form a magnetic fluid with tunable refractive index. The invention provides a method and a system to design a magnetic fluid with a desired refractive index and tune the refractive index of the magnetic fluid. The invention investigates the parameters, or conditions, to design and to tune the refractive index of the magnetic fluid. The measurement of the refractive index also includes a mechanism of total reflection. An example is provided for describing features of the invention as follows.

Figure 1:
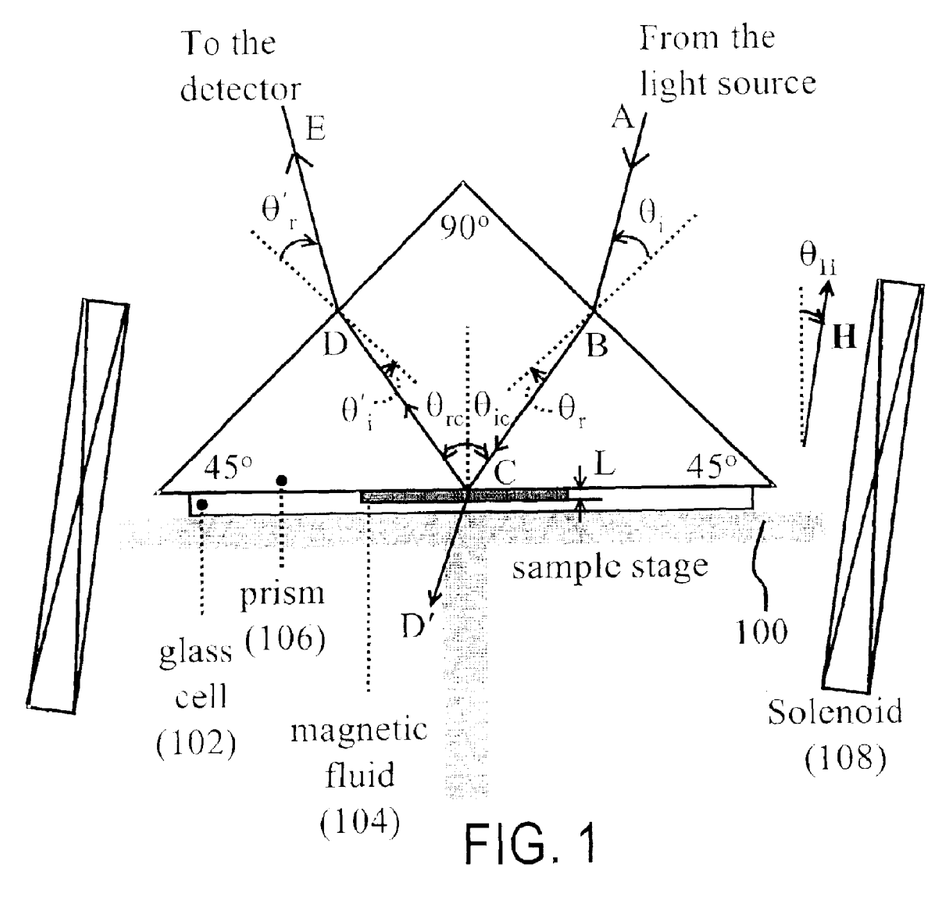
FIG. 1 is a cross-sectional drawing, schematically illustrating a system to measure a refractive index of the magnetic fluid layer.

FIG. 1 is a cross-sectional drawing, schematically illustrating a system to measure a refractive index of the magnetic fluid layer. The magnetic fluids used in the invention for investigation include, for example, water-based, kerosene-based or heptan-based fluids with magnetic particles of $Fe_3O_4$, $MnFe_2O_4$ or $CoFe_2O_4$. In order to investigate what the parameters to design and tune the refractive index, a total reflection is measured since the refraction index is related to the critical angle for total reflection.

The magnetic fluid 104 is injected to a cell 102 in a substrate. The substrate includes a transparent substrate or an opaque substrate, such as a glass substrate or silicone wafer, respectively. The cell 102 is a trench with, for example, an area of 4×4 $mm^2$ and a depth. After injection with the magnetic fluid 104, it is a magnetic fluid layer 104 with a thickness L, equal to the depth. The substrate is held by a sample stage 100. A triangle prism 106 is disposed over the substrate to cover magnetic fluid 104 within the cell 102, wherein the side against the right angle contact with the magnetic fluid 104. Thus, there exists an interface PM between the prism 106 and the magnetic fluid 104. An external magnetic field H can be applied with an adjustable magnetic field direction. The magnetic field H is optionally applied and the intensity and the direction can be varied as desired.

In FIG. 1, when a parallel light ray AB is incident into one side of the prism with an incident angle $\theta_i$, the light experiences the refraction at point B and then reflects from the magnetic fluid 104 at point C. The reflected light has refraction occurring at point D and then leaves the prism 106. The refractive angle at point B is denoted by $\theta_r$, the incident and the reflective angles at point C are $\theta_{ic}$ and $\theta_{rc}$, respectively. The $\theta'_i$ and $\theta'_r$ stand for the incident and the refractive angles at point D. In the case, the total reflection occurs at point C with a condition of $\theta_{ic}=\theta_c$, where $\theta_c$ is the critical angle, at which a total reflection occurs. The refractive index of the magnetic fluid $n_{MF}$ can be derived to be:

$$n_{MF} = \frac{1}{2}(\sqrt{2n_p^2 - 2\sin^2\theta_{it}} - \sqrt{2}\sin\theta_{it}), \qquad (1)$$

where $n_p$ represents the refractive index of the prism 106 and $\theta_{it}$ is the value of $\theta_i$, corresponding to the occurrence of the total reflection on the interface PM. As the $\theta_{ic}$ is smaller than the critical angle $\theta_c$ at the interface PM, portion of the light BC transmits (light CD') through interface PM and the other portion (light CD) reflects from the interface PM. When the $\theta_{ic}$ is larger than $\theta_c$, the total reflection occurs for light BC. Thus, an obvious change in the intensity of light DE can be observed when the angle $\theta_{ic}$ varies passing through $\theta_c$. The variation in $\theta_{ic}$ can be achieved by adjusting the angle $\theta_i$. In this experiment, the intensity of the light DE for various $\theta_i$'s is measured to find the $\theta_{it}$ corresponding to the occurrence of the total reflection at point C.

In the foregoing description, the refractive index of the magnetic fluid is measured based on the total reflection at point C associating with the prism 106. The prism 106 with the refractive index $n_p$ is used to allow the occurrence of total reflection at point C. Since when the total reflection occurs, there is no transmitting portion. The intensity of the out-going light DE saturates with a constant quantity when the angle $\theta_{ic}$ varies passing through $\theta_c$. This allows the critical angle to be determined.

Figure 2:
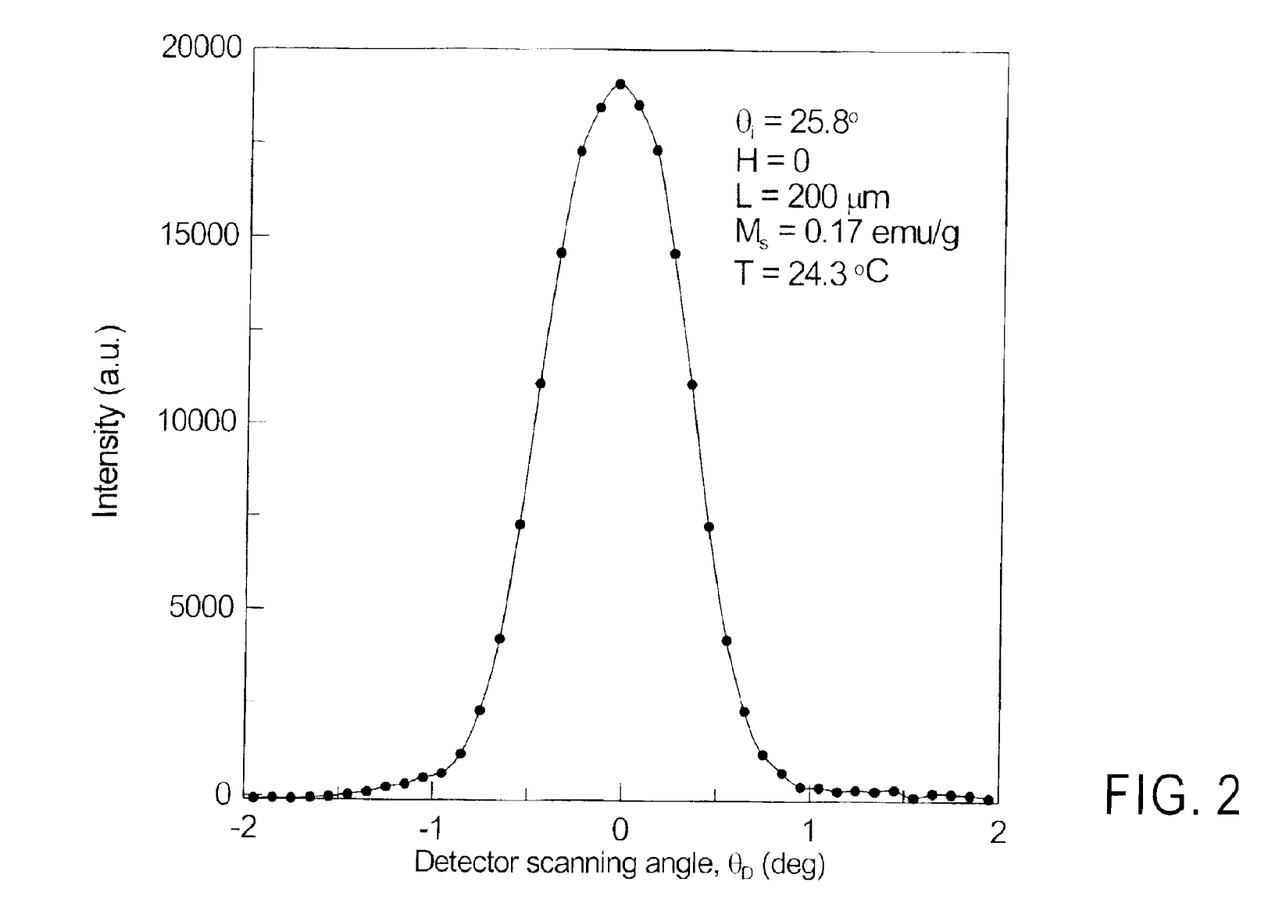
FIG. 2 is a drawing to show how to check the detection system under a measuring condition.

In this work, a parallel light (ray AB) with a beam diameter of 2 mm is, for example, incident into one side of the right angle of the prism, as shown in FIG. 1. The incident angle $\theta_i$ is controlled by using a stepping motor with a resolution of, for example, 0.01°. The prism 106 is made of, for example, ZnSe or others. An optical fiber is used to guide the ray DE to a photo-detector (not shown) to sense the intensity of light. Since the diameter of the optical fiber is much smaller than that of the light ray DE, it is necessary to probe the spatial distribution of the intensity to obtain a real intensity for the light ray DE. To do so, the position of the outward light DE corresponding to a given $\theta_i$ is located through a coarse scan. Then, the distribution of the intensity inside the light beam DE is scanned by finely moving the optical fiber around this position. The scanning angle $\theta_D$ of the optical fiber is controlled by another stepping motor with a resolution of 0.01°. A typical pattern for the spatial distribution of the light ray DE corresponding to a certain incident light ray AB of an incident angle $\theta_i$ is shown in FIG. 2. The symmetry of this curve reveals that the instruments are well aligned through this experiment.

Two kinds of light sources are, for example, employed in this work: one is He—Ne laser, and the other is laser diode. The former one generate parallel lights with a wavelength of 0.6328 $\mu$m, and the later provides an IR light of 1.557 $\mu$m. Since the IR light emitted from the laser diode is divergent instead of parallel, a convex lens is placed in front of the laser diode to produce a parallel light when the originally divergent IR light passes through the lens. The external magnetic field is provided by a pair of solenoids. The direction of the applied magnetic field can be adjusted by tilting the solenoids. The angle formed between the direction of H with respect to the normal line of the film surface is defined as $\theta_H$. The deviation of the applied magnetic field within the sample region is around 0.5%. The temperature is maintained and manipulated by using a circulating water system. The resolution of the temperature is 0.1° C.

Figure 3:
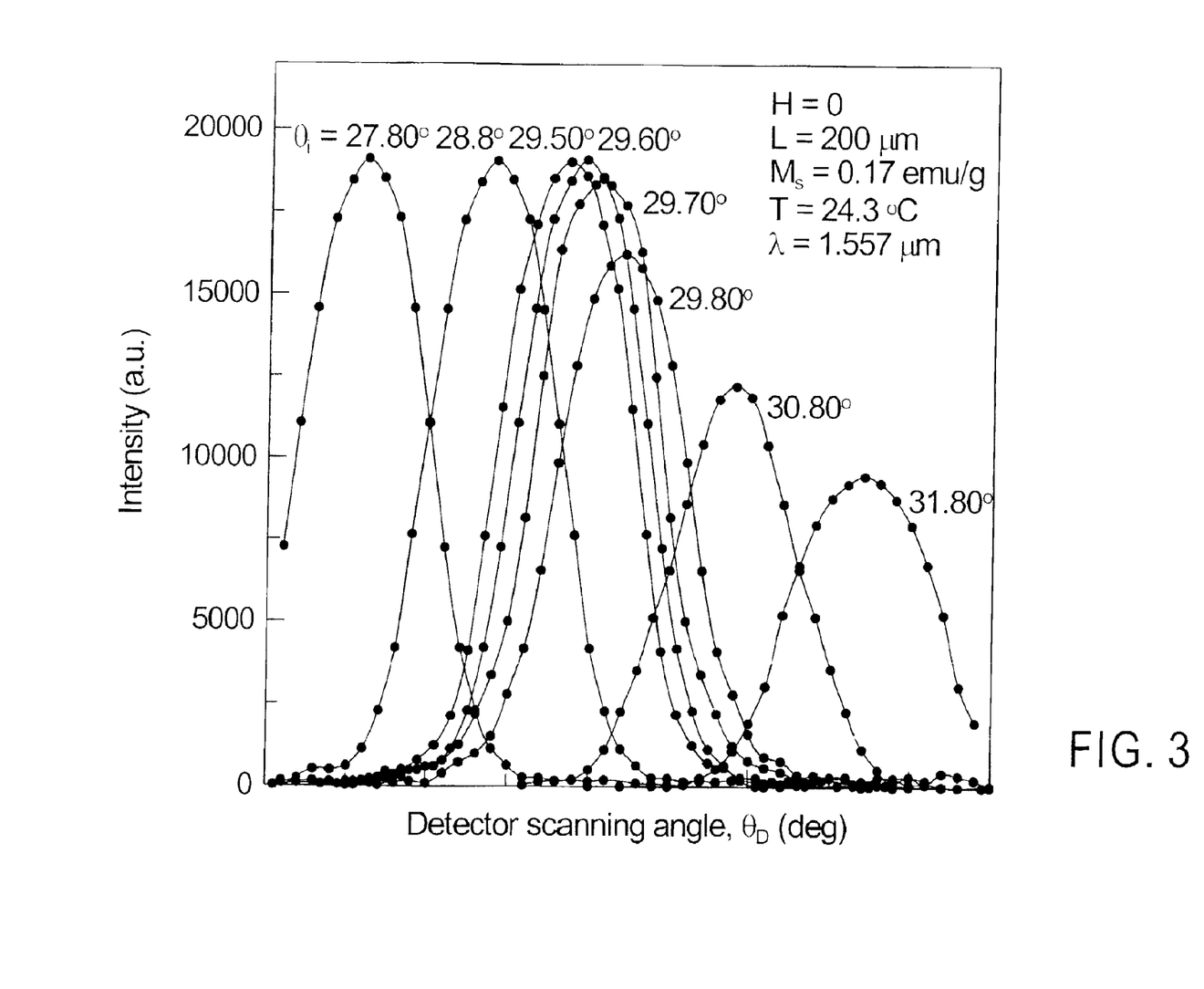
FIG. 3 is a drawing to show the mechanism to find the critical angle for total reflection, used to measure the refractive index.

After verifying the detecting instrument to be working in the proper condition, a searching for the critical angle is performed by varying the incident angle $\theta_i$. The decrease in the $\theta_i$ leads to the increase in the $\theta_{ic}$. When the $\theta_{ic}$ is raised to approach the critical angle $\theta_c$, more and more portion of the incident light BC to the interface PM is reflected. This results in the increase in the intensity for $\theta_i$'s from 31.80° to 29.60°. As the $\theta_i$ is reduced to make $\theta_{ic}$ larger than the critical angle $\theta_c$ on interface PM, the light BC is reflected totally and the intensities of light rays DE nearly remain unchanged for smaller $\theta_i$'s. Hence, the results in FIG. 3 imply that the totally reflection on interface PM occurs at $\theta_i(=\theta_{ii})=29.60°$. With $n_p$ being 2.4739 for $\lambda=1.557$ $\mu$m and based on Eq. (1), the refractive index of the magnetic fluid is 1.3648.

Figure 4:
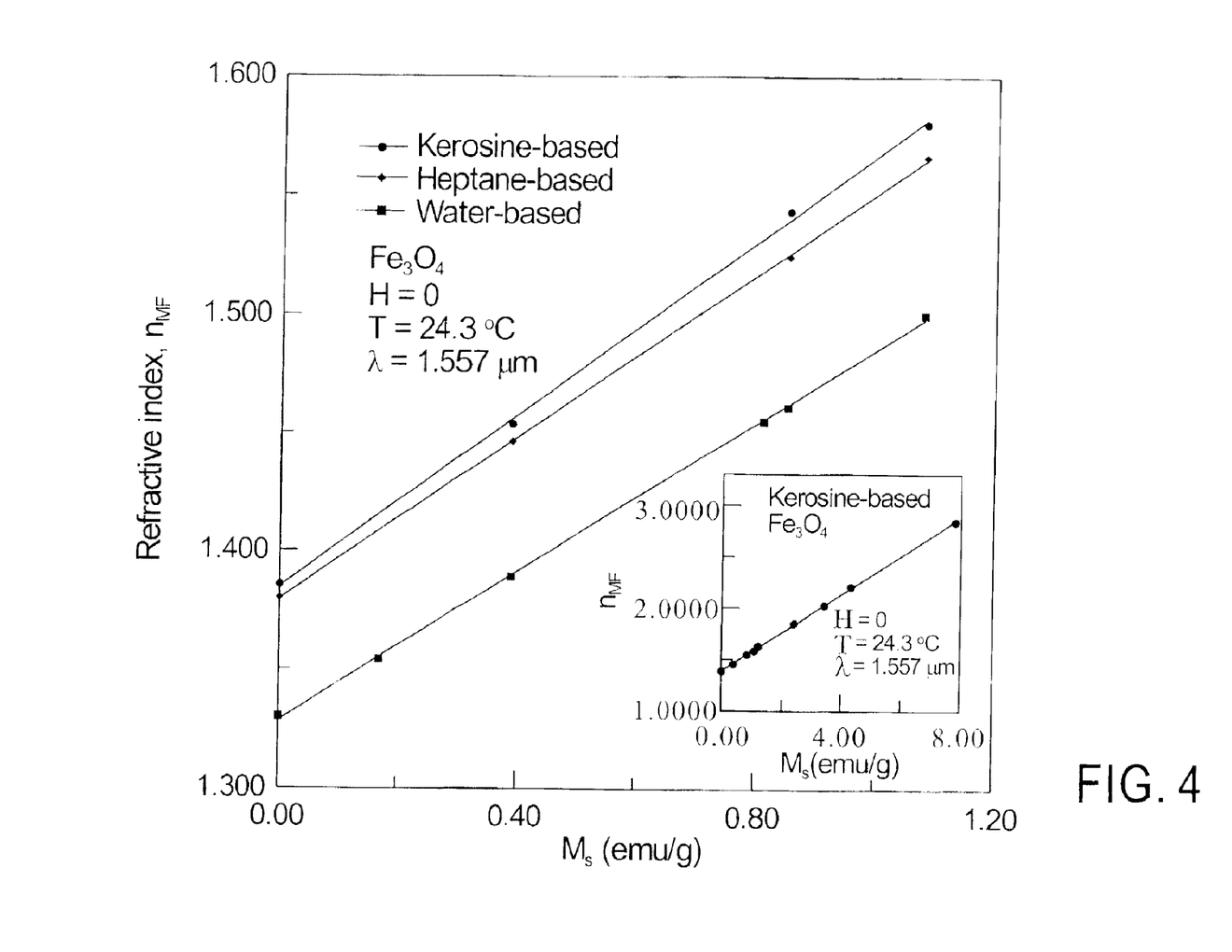
FIGS. 4-6 are drawings, schematically illustrating the possible parameters which can be used to design(tune) the refractive index of the magnetic fluid under zero magnetic field based on the requirement of the application.
Figure 5:
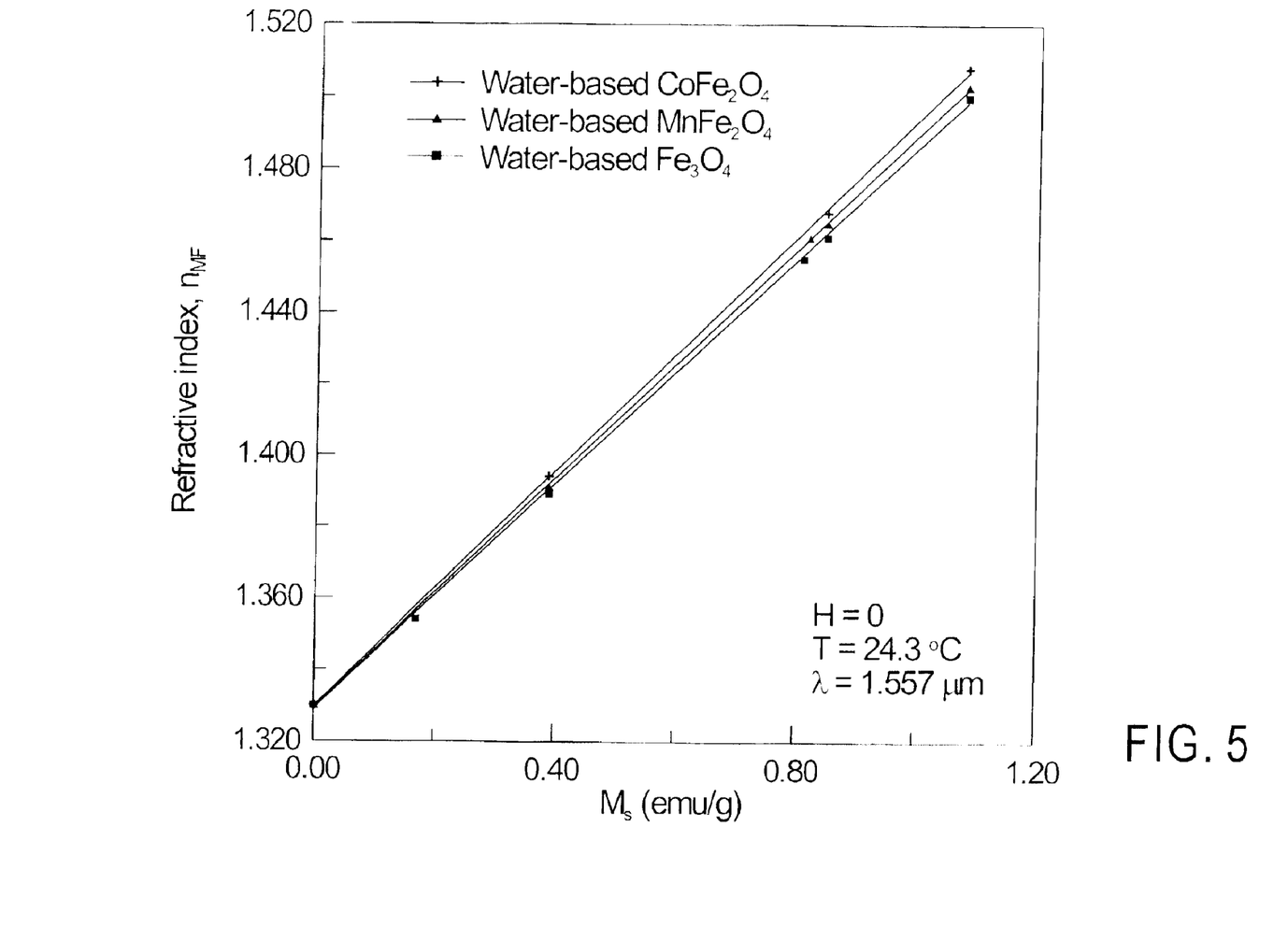
Figure 6:
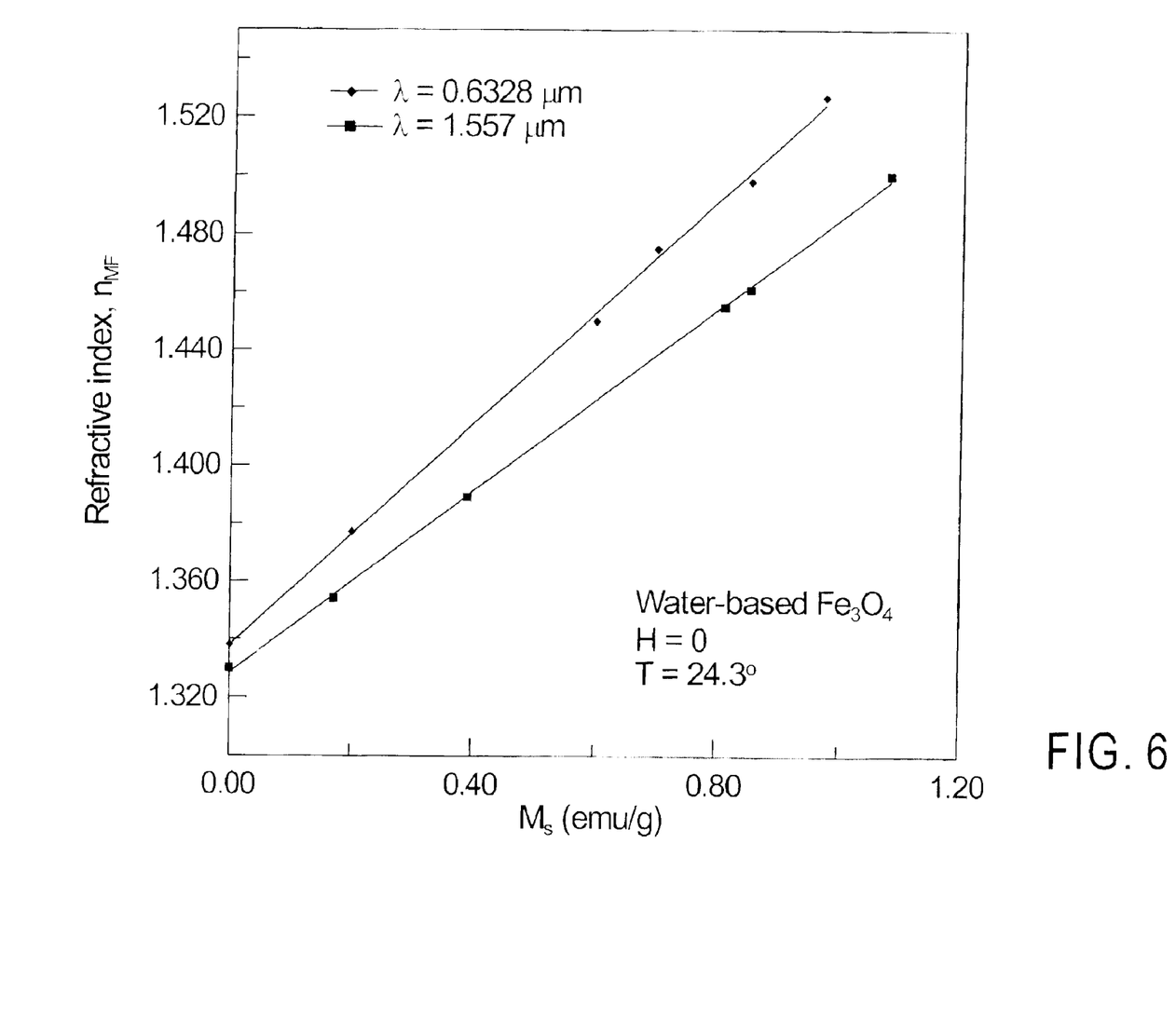

Under the measuring method based on finding the critical angle $\theta_c$, several parameters, or measuring conditions, are investigated, so as to allow the refractive index of the magnetic fluid 104 to be designed at a desirable value per application need. FIGS. 4-6 show the behavior of the refractive indices of magnetic fluids vs. the concentration of the magnetic ingredient for different magnetic carriers, particles, and the wavelength of the used light respectively. Within the range of the concentration of the magnetic fluid used here, the $n_{MF}$ is increased linearly with the increasing $M_s$ via $n_{MF}=\alpha M_s+b$, where $\alpha$ and b depend on either the type of magnetic particles, the carrier of the magnetic fluid, and the wavelength of the used light.

Figure 7:
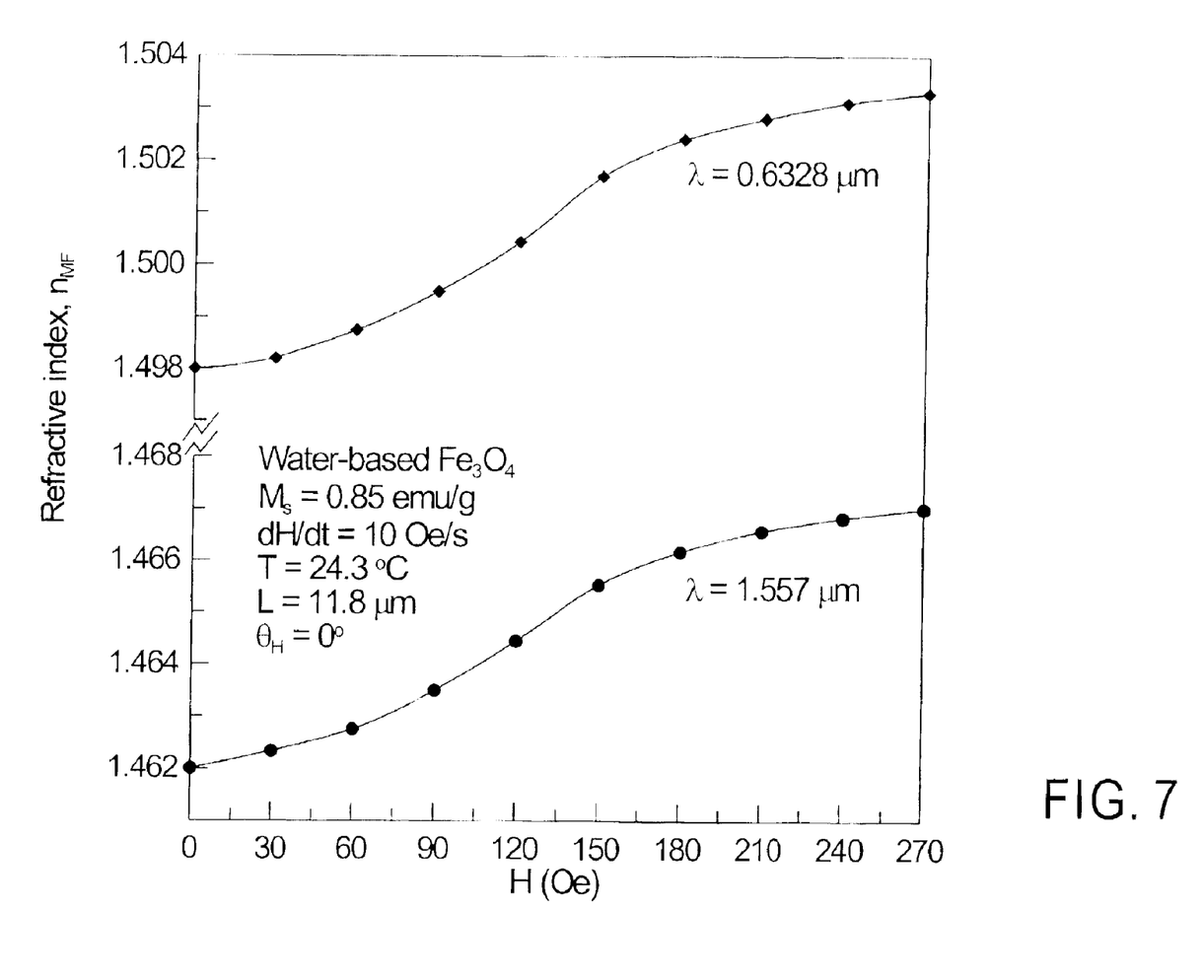
FIG. 7 is a drawing to show the dependency of the refractive index of the magnetic fluid relative to the wavelength of the intended light with the variation of the magnetic field strength.

In FIG. 7, the fact that the refractive index of the magnetic fluid increases with the raising magnetic field was found for the both wavelengths of 0.6328 and 1.557 $\mu$m. The $n_{MF}$ of the magnetic fluid under a given H for the wavelength of 0.6328 $\mu$m is larger than the corresponding $n_{MF}$ for the wavelength of 1.557 $\mu$m. Thus, the refractive index of the magnetic fluid increases as the wavelength of the incoming light decreases.

Figure 8:
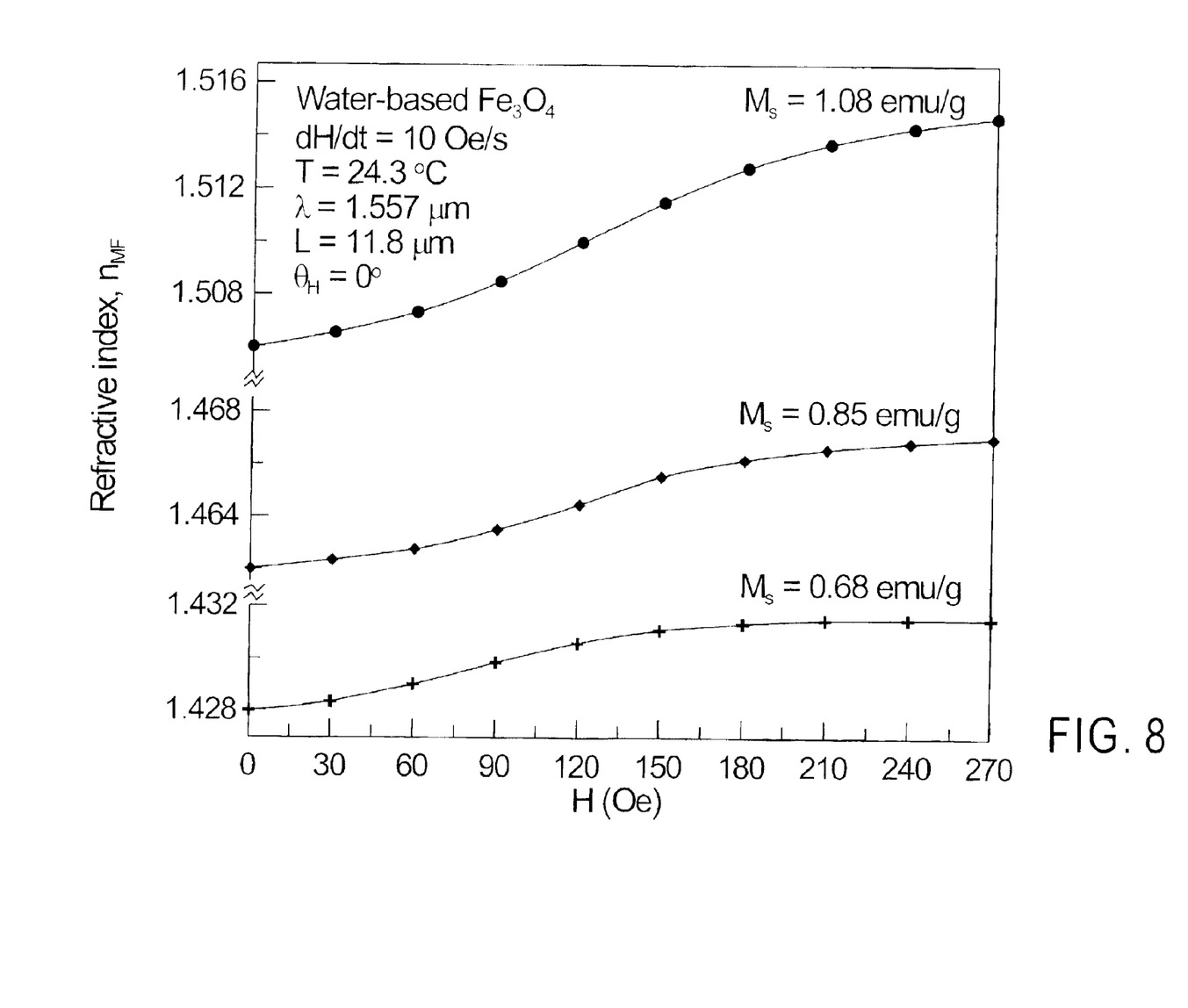
FIGS. 8-13 are drawings, schematically illustrating the possible parameters which can be used to tune the refractive index of the magnetic fluid around its designed value.

For the tunability of the refractive index of magnetic fluid around the designed value, several parameters, or measuring conditions, are investigated, and are shown in FIG. 8-FIG. 13. In FIG. 8, for a given $M_s$, the $n_{MF}$ increases significantly as the magnetic field H raises from zero up to 150 Oe, and then almost becomes saturated under H's higher than 150 Oe. The $n_{MF}$-H curve is shifted to the region with larger $n_{MF}$'s for a higher concentration of magnetic fluid. Also and, the magnetic fluid 104 with a higher concentration exhibits a larger variation in $n_{MF}$ with the varying H.

Figure 9:
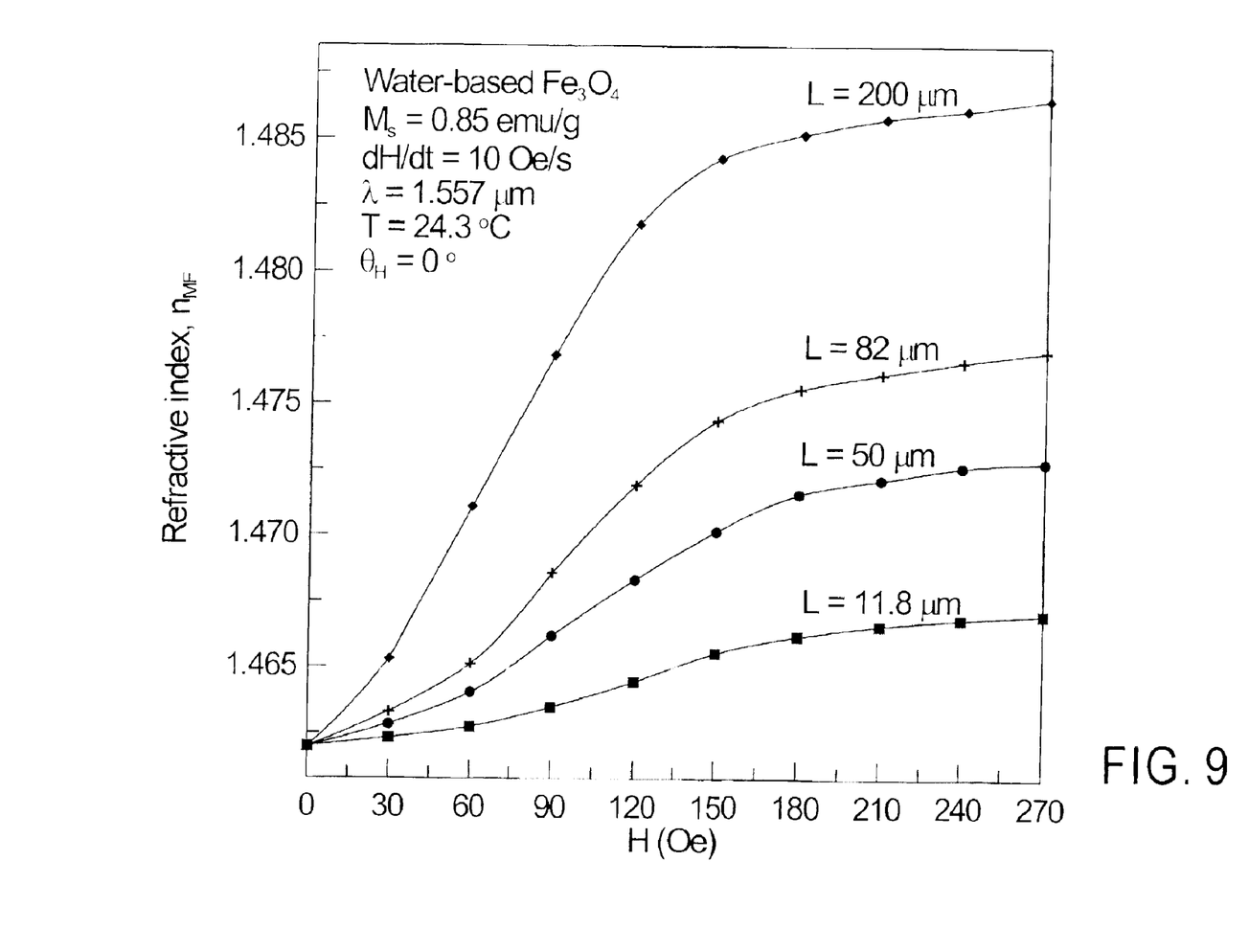

In FIG. 9, for a given L, for example, 11.8 $\mu$m, the $n_{MF}$ increases significantly as the H raises from zero up to 150 Oe, and then almost becomes saturated under H's higher than 150 Oe. When the L is enlarged, the zero-field $n_{MF}$ still remains unchanged as compared with that of a thinner film. However, the saturated value of $n_{MF}$ becomes larger as the thickness of a magnetic fluid film is increased. Furthermore, the magnetic fluid 104 with a bigger L exhibits a larger variation in $n_{MF}$ with the varying H.

Figure 10:
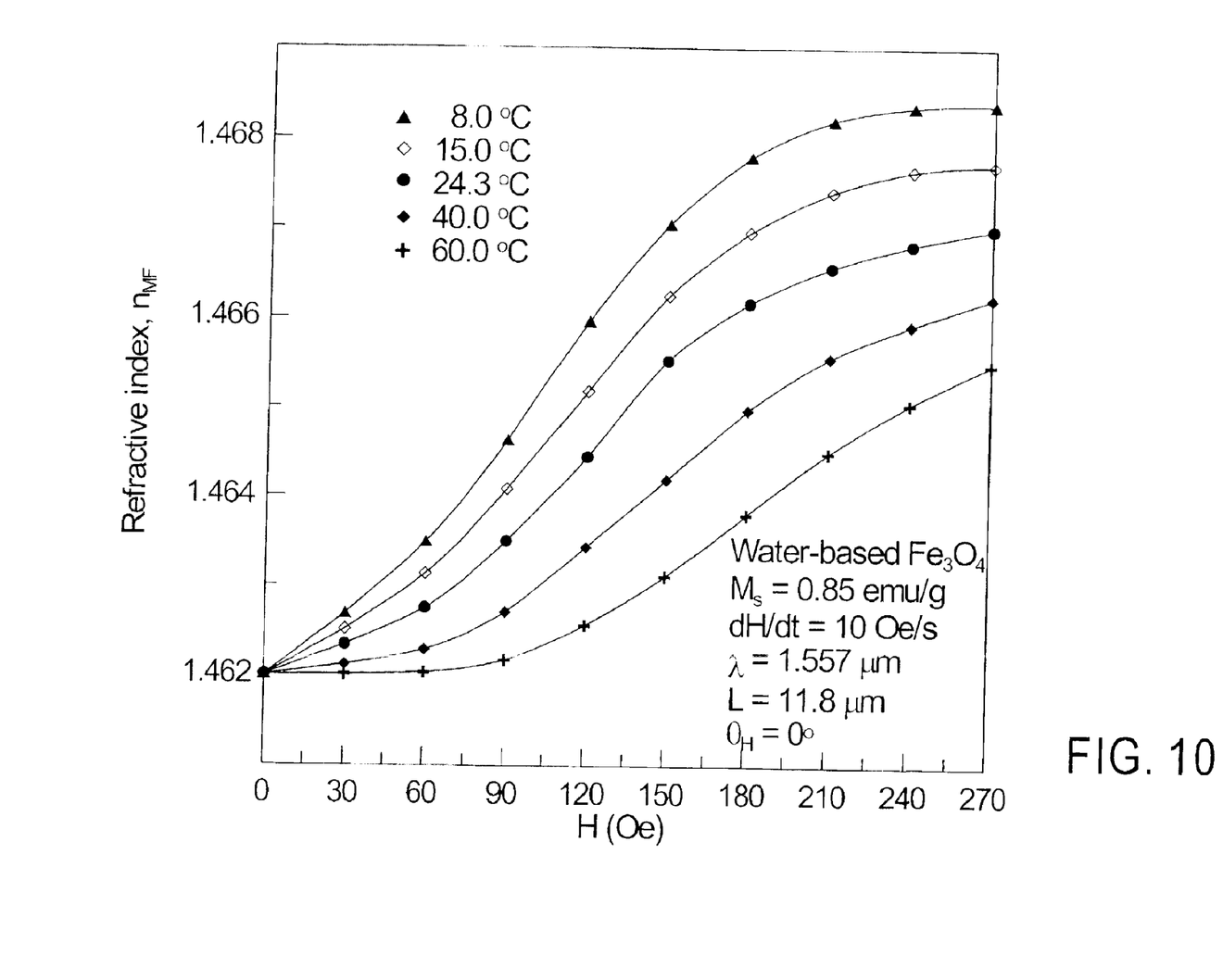

In FIG. 10, under a zero field, the $n_{MF}$ hardly changes with the temperature from 8.0 to 60.0° C. When the H is applied perpendicularly to the magnetic fluid film at a fixed temperature, the $n_{MF}$ increases to a certain value. It was found this value of $n_{MF}$ is reduced as the temperature is raised. For example, the $n_{MF}$ of the magnetic fluid film at 8.0° C. under zero field is 1.4620 and becomes 1.4660 under 120 Oe. While at 60.0° C. under 120 Oe, the $n_{MF}$ is reduced down to 1.4626. This reveals that the effects of the magnetic field and the temperature on the variation in the refractive index of the magnetic fluid compensate with each other.

Figure 11:
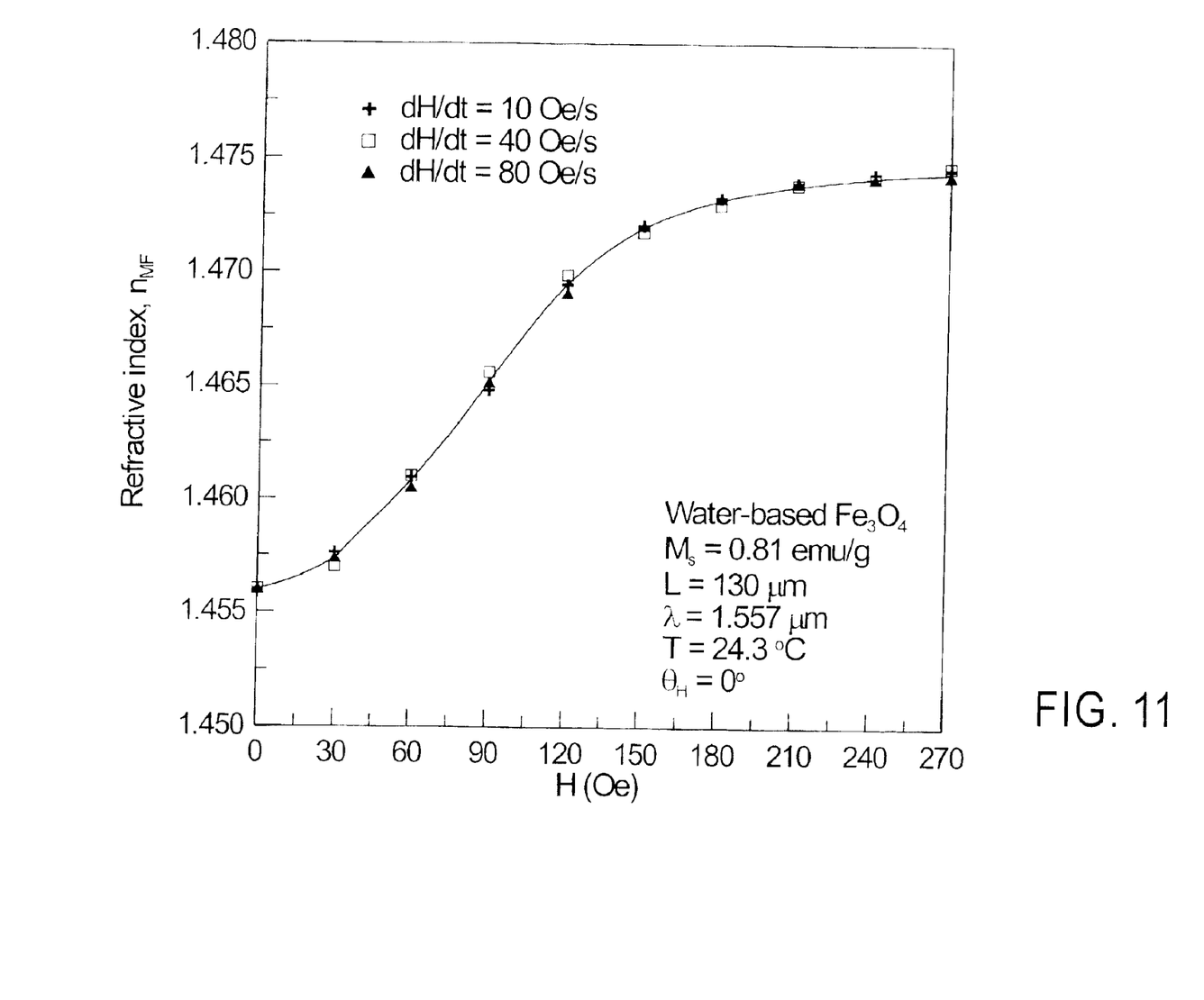

In FIG. 11, the $n_{MF}$-H curves of the magnetic fluid at various sweep rates, dH/dt. overlap. This implies that the variation in the $n_{MF}$ is almost independent of the sweep rate of the magnetic field.

Figure 12:
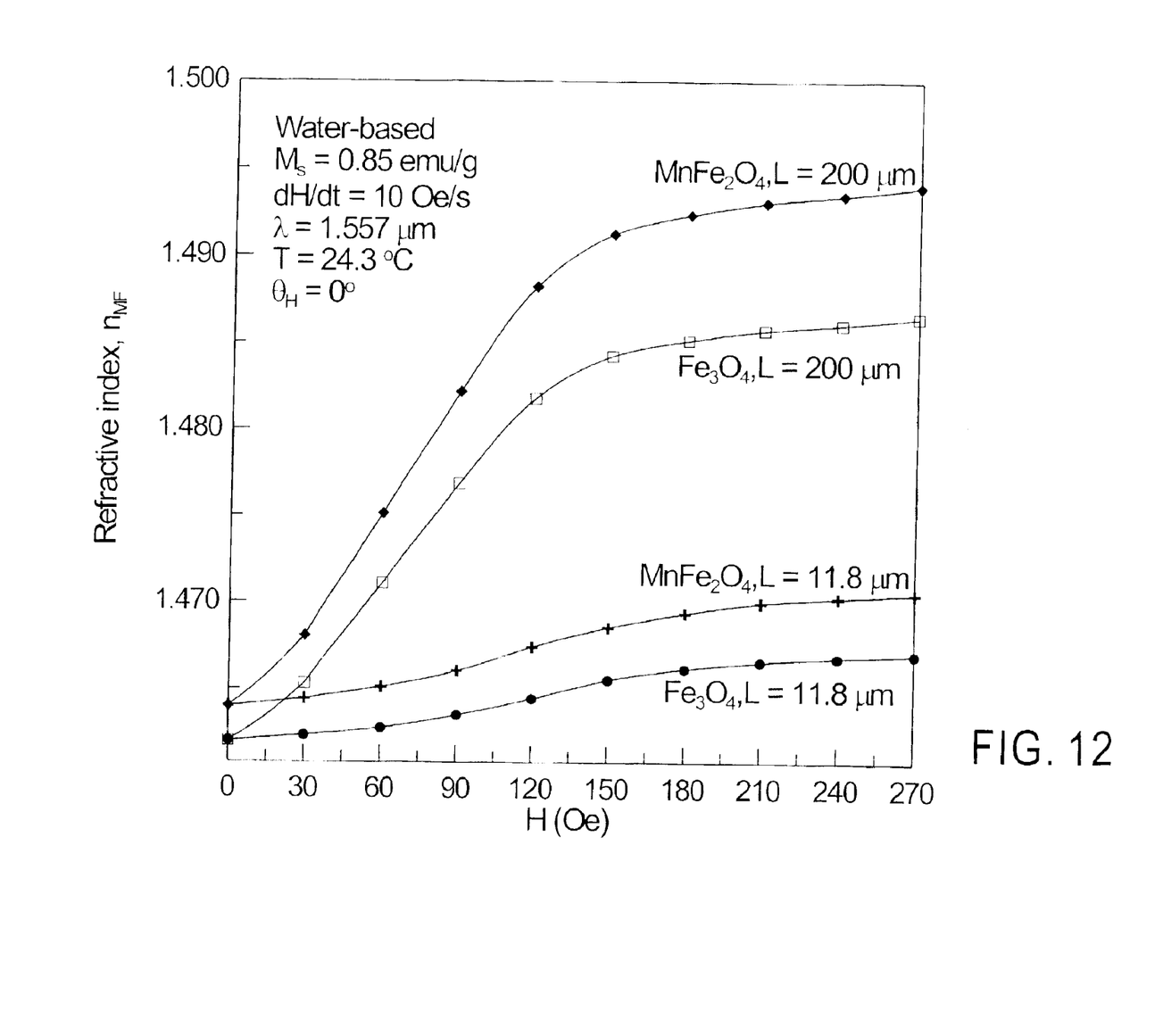

In FIG. 12, a similar trend is observed for the $n_{MF}$-H curves for the magnetic fluid film containing various kinds of magnetic particles ($MnFe_2O_4$ and $Fe_3O_4$, respectively): the higher the H, the larger the $n_{MF}$. However, for a given film thickness, the $n_{MF}$-H curve moves to the region of larger $n_{MF}$ for the magnetic fluid of $MnFe_2O_4$ in compare to that of $Fe_3O_4$.

Figure 13:
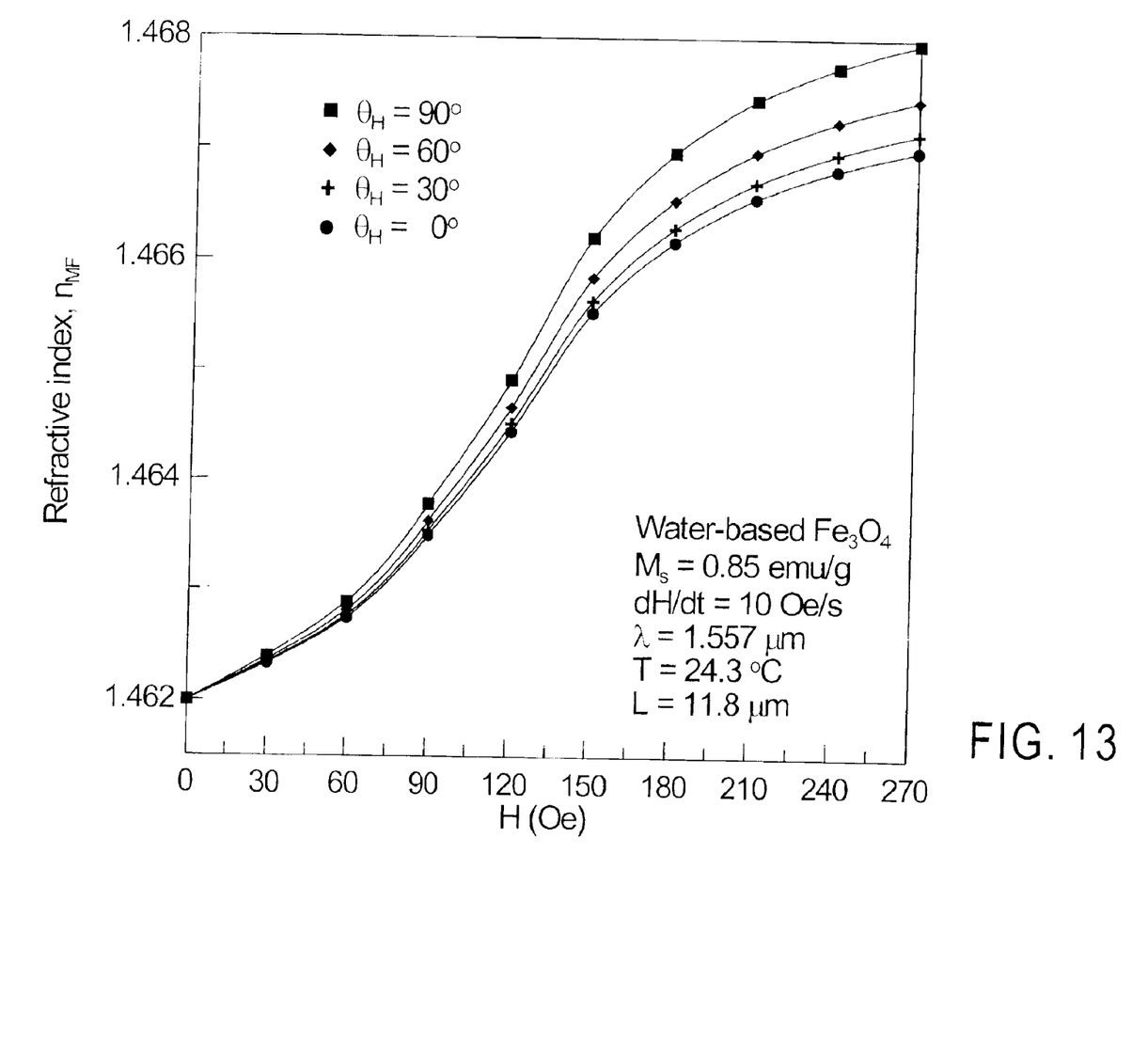

In FIG. 13, a similar behavior was found for the $n_{MF}$-H curves of various angle $\theta_H$. For a given field strength, the $n_{MF}$ is raised when the magnetic field rotated from the direction along the normal line of the film surface to that perpendicular to the normal line.

The parameters or operation conditions in the foregoing investigations allow the refractive index to be designed and to be tunable. When a magnetic fluid layer with a specific refractive index is desired in the actual design, the refractive index $n_{MF}$ can be achieved by designing and tuning it under consideration of the available parameters. For example, if one magnetic fluid layer 104 is desired to have a thickness L and is operated by a wavelength, the desired refractive index can then be designed and tuned by, for example, the carrier, the type of magnetic particles, concentration, applied magnetic field, and so on.

In summary, the invention introduces a magnetic fluid that its refractive index can be designed at a desired quantity based on the need of the application.

The invention also introduces a magnetic fluid with a tunable refractive index from the designed value. It improves the facilitations of the magnetic fluid in various applications.

In the invention, the mechanism of total reflection is applied for measuring the refractive index of the magnetic fluid, whereby the refractive index can be effectively designed and tuned to the desired quantity.

It will be apparent to those skilled in the art that various modifications and variations can be made to the structure of the present invention without departing from the scope or spirit of the invention. In view of the foregoing, it is intended that the present invention covers modifications and variations of this invention provided they fall within the scope of the following claims and their equivalents.

What is claimed is:

1. A method for designing a magnetic fluid with a desired refractive index under zero field for an application, wherein the method comprising:

determining a wavelength of a light to be used in the application;

determining in intended first refractive index, based on the application;

selecting a carrier as a fluid base, wherein the fluid base has a second refractive index less than the first refractive index;

selecting a type of magnetic particle;

adjusting a volume concentration of the magnetic particles, such that the magnetic fluid has a refractive index about equal to the first refractive index.

2. A method for forming a magnetic fluid layer with a tunable refractive index, wherein an external variable magnetic field is optionally applied, the method comprising:

providing a magnetic fluid, which comprises a fluid base and a magnetic ingredient;

injecting the magnetic fluid into a substrate cell to have the magnetic fluid layer; and tuning the refractive index of the magnetic fluid layer wider considering at least one of a plurality of parameters consisting of:

a concentration of magnetic particles of the magnetic ingredient;

an externally applied magnetic field;

a magnetic field direction;

a strength of the applied magnetic field associating with a thickness of the magnetic fluid layer;

a strength of the applied magnetic field associating with a temperature; and a strength of the applied magnetic field associating with a sweep rate of the magnetic field.

* * * * *